United States Patent [19]

Sasaki et al.

[11] Patent Number: 4,915,115
[45] Date of Patent: Apr. 10, 1990

[54] ULTRASONIC IMAGING APPARATUS FOR DISPLAYING B-MODE AND DOPPLER-MODE IMAGES

[75] Inventors: Hiroshi Sasaki; Takahisa Okazaki, both of Ootawara, Japan

[73] Assignee: Kabushiki Kaisha Toshiba, Kawasaki, Japan

[21] Appl. No.: 7,355

[22] Filed: Jan. 27, 1987

[30] Foreign Application Priority Data

Jan. 28, 1986 [JP] Japan ................................. 61-14632

[51] Int. Cl.⁴ .............................................. A61B 8/00
[52] U.S. Cl. ........................... 128/660.05; 128/662.04
[58] Field of Search ................ 73/618, 620, 221, 625, 73/626, 632, 633, 639, 861.25; 128/660, 661, 662, 663, 660.05, 662.04; 310/334

[56] References Cited

U.S. PATENT DOCUMENTS

| | | | |
|---|---|---|---|
| 4,097,835 | 6/1978 | Green | 73/626 |
| 4,141,347 | 2/1979 | Green et al. | 128/2 V |
| 4,234,940 | 11/1980 | Iinuma | 367/105 |
| 4,245,321 | 1/1981 | Gennetten | 364/521 |
| 4,276,491 | 6/1981 | Daniel | 128/660 |
| 4,283,765 | 8/1981 | Rieger | 364/521 |
| 4,407,293 | 10/1983 | Suarez, Jr. et al. | 73/633 |
| 4,446,395 | 5/1984 | Hadjicostis | 128/660 |
| 4,459,853 | 7/1984 | Wiwa et al. | 128/660 |
| 4,528,854 | 7/1985 | Shimazaki | 73/626 |
| 4,542,653 | 9/1985 | Liu | 73/626 |
| 4,542,746 | 9/1985 | Takamizawa | 128/660 |
| 4,550,606 | 11/1985 | Drost | 73/626 |
| 4,680,499 | 7/1987 | Umemura et al. | 310/334 |
| 4,714,846 | 12/1987 | Pesque et al. | 310/334 |

OTHER PUBLICATIONS

Biomedical Ultrasonics, P. N. T. Wells, Academic Press, New York, N.Y., 1977, pp. 49–53, 57, 58.

Primary Examiner—Francis Jaworski
Assistant Examiner—George Manuel
Attorney, Agent, or Firm—Finnegan, Henderson, Farabow, Garrett, and Dunner

[57] ABSTRACT

An ultrasonic imaging apparatus includes an ultrasonic transducer for transmitting/receiving a high-frequency ultrasonic wave for obtaining a B-mode image and a low-frequency ultrasonic wave for obtaining a Doppler-mode image, a transmission circuit for driving the ultrasonic transducer in B and Doppler modes so as to output an ultrasonic beam therefrom, a reception circuit for processing a high-frequency echo signal corresponding to the B mode and a low-frequency echo signal corresponding to the Doppler mode, and for outputting a B-mode image signal and a Doppler-mode image signal, and a display circuit for displaying the B- and Doppler-mode image signals from the reception circuit as a tomographic image of an object to be measured and blood flow speed data.

8 Claims, 5 Drawing Sheets

ULTRASONIC IMAGING APPARATUS FOR DISPLAYING B-MODE AND DOPPLER-MODE IMAGES

BACKGROUND OF THE INVENTION

The present invention relates to an ultrasonic imaging apparatus capable of displaying B- and Doppler-mode images.

Ultrasonic imaging apparatuses are widely used in various industrial fields. In particular, development of ultrasonic imaging apparatuses as ultrasonic diagnostic apparatuses has been significant in the medical field. A recent ultrasonic diagnostic apparatus can display both a tomographic image (i.e., a B-mode image) and a blood flow image (i.e., a Doppler-mode image). Such a conventional ultrasonic diagnostic apparatus is used for cardiac or carotid diagnosis. Therefore, both a tomographic image of a portion to be examined, and a blood flow state of the blood vessel system shown in the tomographic image can be displayed.

There are two types of conventional ultrasonic imaging apparatus capable of displaying the mode images described above. The first apparatus has a B-mode ultrasonic probe and a Doppler mode single probe in an acoustic medium. In this apparatus, the B-mode ultrasonic probe is driven by a 7.5- or 10-MHz RF drive signal to acquire high-resolution B-mode image data. The Doppler mode single probe is driven by a 3.5-MHz low frequency signal and outputs a Doppler signal for measuring a blood flow speed.

The second apparatus uses an electronic linear ultrasonic probe. Electronic scanning is performed to obtain a B-mode image, and an ultrasonic beam is obliquely emitted to obtain a Doppler mode image.

The first conventional ultrasonic imaging apparatus requires two types of probes thus complicating the overall structure of the probe, thereby degrading reliability and posing maintenance problems. The second conventional ultrasonic imaging apparatus is driven at an identical frequency in the B and Doppler modes. Therefore, the B- and Doppler-mode images having opposite frequency characteristics cannot be produced in an optimal state. More specifically, the resolution of the B-mode image can be improved at high drive frequencies. However, the Doppler signal is greatly attenuated at high drive frequencies, and a good Doppler-mode image cannot be obtained. Also, as the Doppler shift is proportional to the blood flow speed, a detectable highest flow speed is limited.

SUMMARY OF THE INVENTION

It is an object of the present invention to provide an ultrasonic imaging apparatus capable of producing a high-resolution B-mode image and allowing Doppler measurement of a high-speed fluid without complicating the probe structure.

According to the present invention, the ultrasonic imaging apparatus includes a single ultrasonic transducer in which first and second ultrasonic transducer elements are integrally assembled, the first ultrasonic transducer element being driven at a high frequency so as to produce a B-mode image and the second ultrasonic transducer element being driven at a low frequency so as to obtain a Doppler image. The first and second transducer elements are selectively switched by a switching circuit to produce a high-frequency signal corresponding to the B-mode image and the low-frequency signal corresponding to the Doppler-mode image. The high- and low-frequency signals are separated by a filter circuit and are respectively input to an image signal processor and a Doppler signal processor. These frequency signals are then processed by these processors. Output signals from the processors are input to a display circuit and are displayed as a tomographic image of a monitored portion and its fluid speed data image.

DETAILED EXPLANATION OF THE PREFERRED EMBODIMENTS

Figure 1:
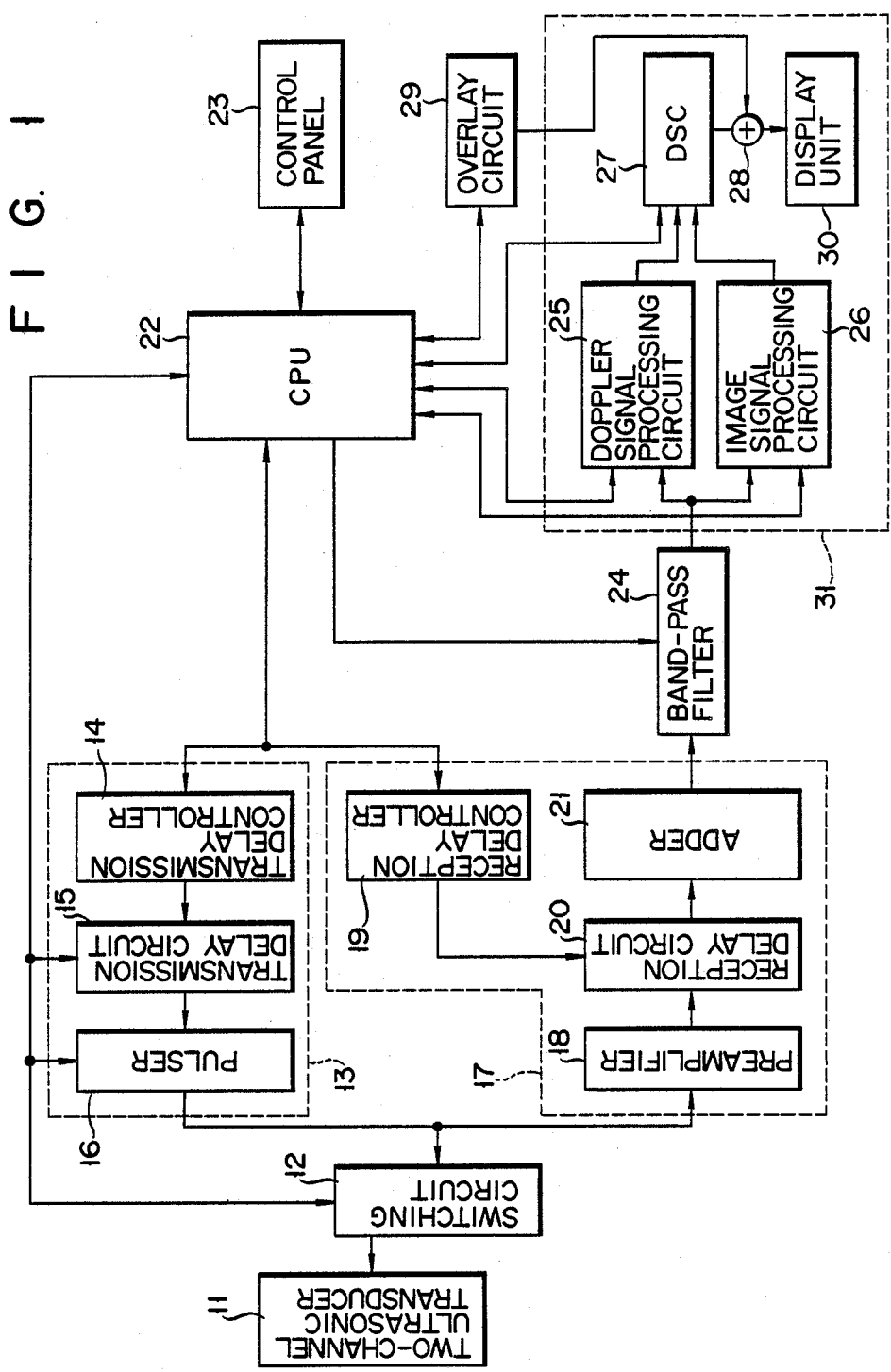
FIG. 1 is a block diagram of an ultrasonic imaging apparatus according to an embodiment of the present invention.
Figure 2:
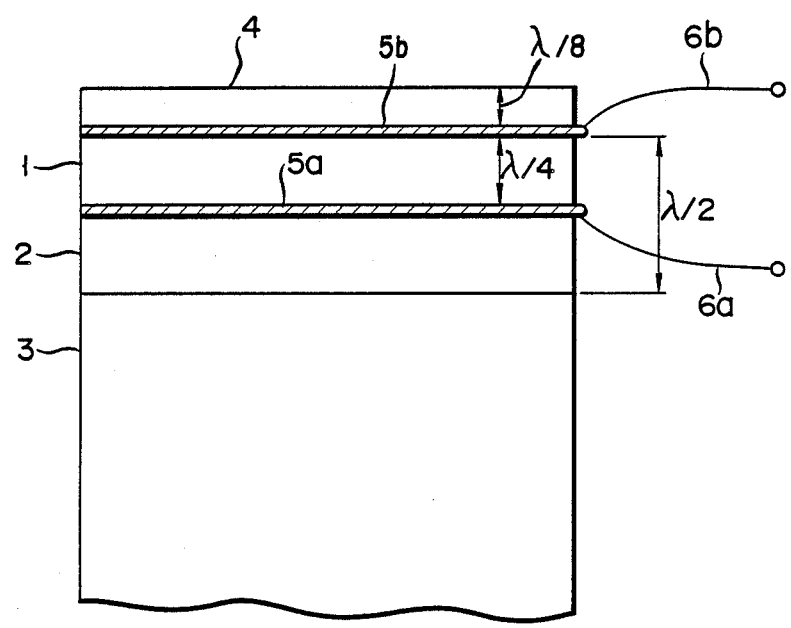
FIG. 2 is a sectional view of an ultrasonic transducer.
Figure 5:
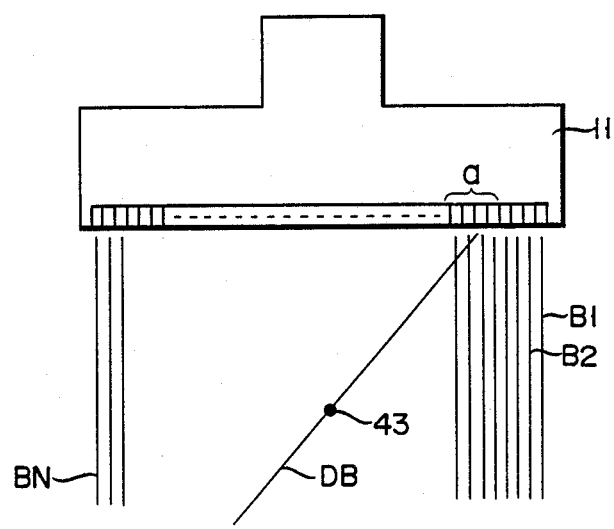
FIG. 5 is a view showing ultrasonic linear scanning by the ultrasonic transducer.

An ultrasonic transducer in an ultrasonic imaging apparatus is shown in FIG. 1 as two-channel ultrasonic transducer 11. The ultrasonic transducer 11 comprises a plurality of ultrasonic transducer elements (a) arranged in a line, as shown in FIG. 5. Each of the ultrasonic transducer elements (a) is constructed as shown in FIG. 2. A piezo-electric ceramic layer 1 has thickness resonance frequency $2f0$ and a thickness (e.g., $\lambda/4$ where $\lambda$ is a wavelength at resonance frequency $f0$) corresponding to about ½ the wavelength at frequency $2f0$. Electrodes 5a and 5b are respectively formed on both major surfaces of ceramic 1. Back load-ceramic 2 is formed on the surface of electrode (5a) which opposes its surface contacting ceramic 1. Load-ceramic 2 serves as a high impedance backing layer. Load-ceramic 2 has substantially the same thickness (e.g., $\lambda/4$) as that of ceramic 1. Sound absorbing member 3 made of, e.g., a rubber material having a low sound impedance is formed on the surface of load-ceramic 2 which opposes its surface contacting electrode 5a.

Acoustic matching layer 4 of epoxy resin is formed on the surface of electrode 5b. Layer 4 has a thickness (e.g., $\lambda/8$) corresponding to ¼ the wavelength at frequency $2f0$. Electrodes 5a and 5b are respectively connected to lead lines 6a and 6b.

In two-channel ultrasonic transducer 11 having the arrangement described above, a composite layer of ceramic 1 and load-ceramic 2 having total thickness $\lambda/2$ serves as an ultrasonic probe having resonance frequency $2f0$. Acoustic matching layer 4 having thickness $\lambda/8$ serves as a probe having resonance frequency $f0$.

Figure 3:
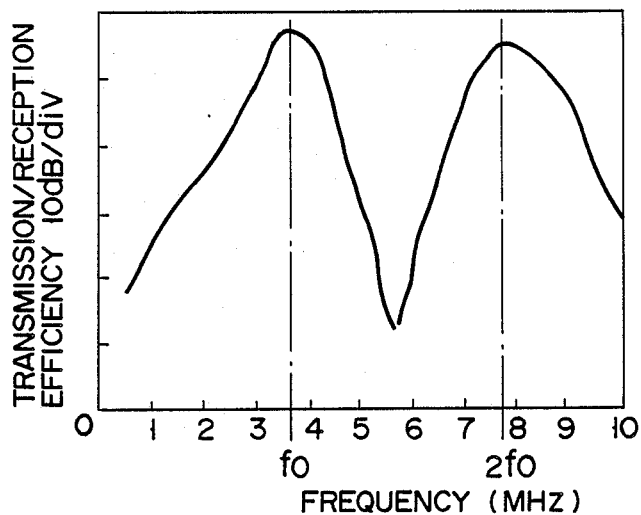
FIG. 3 is a graph showing the frequency characteristics of the ultrasonic transducer in FIG. 2.
Figure 4:
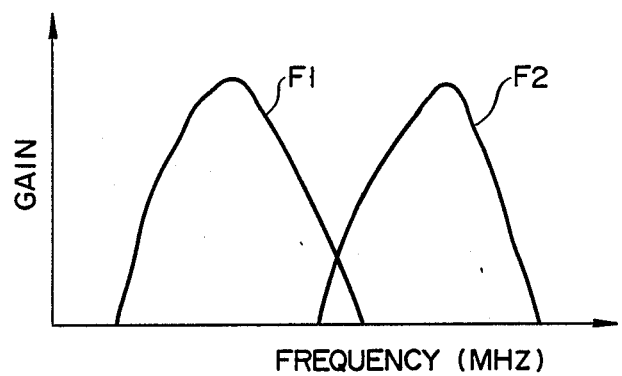
FIG. 4 is a graph showing the frequency characteristics of a filter used in the apparatus of FIG. 1.

Ultrasonic transducer 11 shown in FIG. 2 has the frequency characteristics shown in FIG. 3. As is apparent from these characteristic curves, two frequency signals having center frequencies of 3.7 MHz and 7.8 MHz provide maximum transmission/reception efficiency of transducer 11. In a conventional single channel transducer, matching between a piezo-electric member and a sound field medium is achieved at frequency f0 corresponding to λ/4, and transmission/reception efficiency at 2f0 is degraded. However, according to the two-channel transducer of the present invention, sufficiently high transmission/reception efficiency of the signal having frequency 2f0 can be achieved.

As shown in FIG. 1, ultrasonic transducer 11 is connected to transmission circuit 13 and reception circuit 17 through switching circuit 12. Transmission circuit 13 includes pulser 16 for sending a high-voltage drive pulse to transducer 11 through switching circuit 12. The input terminal of pulser 16 is connected to the output terminal of transmission delay circuit 15 to output a drive pulse in response to a delay signal generated by transmission delay circuit 15. The delay time of delay circuit 15 is determined according to an output from transmission delay controller 14 which corresponds to the scanning direction and focusing position of the ultrasonic beam.

Reception circuit 17 includes preamplifier 18 for amplifying an echo signal sent from ultrasonic transducer 11 through switching circuit 12, and reception delay circuit 20 connected to the output terminal of preamplifier 18. Reception delay controller 19 is connected to the control input terminal of reception delay circuit 20, and the output terminal of reception delay circuit 20 is connected to adder 21. The output terminal of adder 21 is connected to display circuit 31 through band-pass filter 24.

Band-pass filter 24 has two band-pass filter characteristics F1 and F2 having center frequencies f0 and 2f0. The center frequencies of filter 24 are switched for every rate pulse under the control of CPU 22. More specifically, characteristics F2 are selected to filter the B-mode signal, and characteristics F1 are selected to filter the Doppler mode signal.

Display circuit 31 is connected to Doppler signal processing circuit 25 and image signal processing circuit 26, both of which are connected to the output of band-pass filter 24. The output terminals of processing circuit 25 and processing circuit 26 are connected to the input of digital scan converter (DSC) 27. The output terminal of digital scan converter 27 is connected to adder 28. Adder 28 is also connected to the output of overlay circuit 29 to superpose the image signal from converter 27 on information from overlay circuit 29. The superposed image is displayed on monitor 30.

CPU 22 has a function for controlling the entire operations of the ultrasonic imaging apparatus. CPU 22 is connected to switching circuit 12, transmission delay controller 14, reception delay controller 19, band-pass filter 24, overlay circuit 29, Doppler signal processor 25, image signal processing circuit 26, and digital scan converter 27.

The operation of the ultrasonic imaging apparatus will be described below. In order to produce a B-mode image, program information for executing the linear scan as shown in FIG. 5 is sent from CPU 22 to transmission delay controller 14. Controller 14 sets the delay time required for first steering and focusing of the ultrasonic beam in transmission delay circuit 15. Delay circuit 15 sends to pulser 16 a delay signal corresponding to the delay time set in delay circuit 15.

Pulser 16 sends a high-voltage drive pulse to switching circuit 12 in response to the delay signal. In this case, switching circuit 12 is switched to supply drive pulses to the ultrasonic transducer elements corresponding to beam B1 of FIG. 5 in response to a switching signal from CPU 22. In this case, drive pulses are supplied to electrodes 5a and 5b of the ultrasonic element through lead lines 6a and 6b shown in FIG. 2. Upon driving of ultrasonic transducer 11 in response to the drive pulse, transducer 11 emits beam B1 onto an object to be examined.

When an echo from the object is incident on ultrasonic transducer 11, echo signals are input to preamplifier 18 in reception circuit 17 through switching circuit 12. The echo signals amplified by preamplifier 18 are delayed by reception delay circuit 20. Delay circuit 20 delays the input signal by a delay time corresponding to the transmission delay time from reception delay controller 19.

The echo signals from reception delay circuit 20 are input to adder 21 and added thereby. The sum signal is output as a B-mode image signal to band-pass filter 24. Since band-pass filter 24 has filter characteristics F2 determined by a signal from CPU 22, the B-mode signal is input to image signal processing circuit 26 through filter 24. The B-mode signal amplified by image signal processing circuit 26 is input to and converted by digital scan converter 27 into a television signal. The television signal is input to and displayed as a one-line B-mode image on monitor 30.

Figure 6:
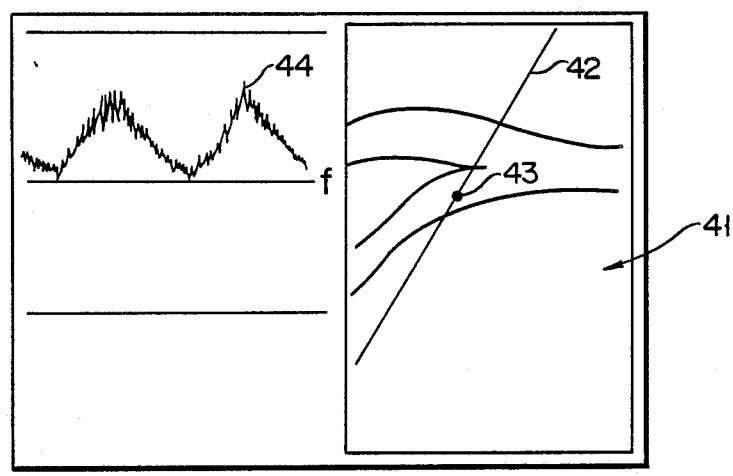
FIG. 6 is a view showing a monitor display screen.

When the first line B1 is displayed, ultrasonic transducer 11 is driven in response to the drive pulse to display the second line B2. In this case, the delay times of transmission and reception delay circuits 15 and 20 and switching circuit 12 are switched to correspond to line B2. In this manner, when the object is scanned with an ultrasonic beam from line B1 to line B2, the tomographic image of the scanned portion, that is, B-mode image 41 is displayed on monitor 30, as shown in FIG. 6.

Control panel 23 is operated by the operator while he observes the B-mode image. A direction of the portion requiring blood flow measurement, e.g., a direction of Doppler beam dB, and a sampling position are set. These pieces of information are input to overlay circuit 29 through CPU 22. Doppler beam direction information and sampling position information are input to monitor 30 through adder 28, and the direction and position are indicated by a cursor. When the desired direction and position are visually confirmed on the monitor display, the Doppler mode is set. In this case, CPU 22 supplies optimal delay time information and optimal drive pulse frequency information to transmission delay controller 14. More specifically, delay information for emitting an ultrasonic beam at angle θ, e.g., drive pulse frequency information having a center frequency of 3.7 MHz is input to transmission delay controller 14.

Transmission delay controller 14 causes transmission delay circuit 15 to set delay time for allowing emission of an ultrasonic beam at angle θ from ultrasonic transducer 11. Delay controller 14 also supplies a signal having a center frequency of 3.7 MHz to delay circuit 15. When the output signal from delay circuit 15 is input to pulser 16, pulser 16 supplies a drive pulse having a center frequency of 3.7 MHz to transducer 11 through switching circuit 12. The ultrasonic transducer elements (a) of transducer 11 are driven in response to the drive pulses. In this case, acoustic matching layer 4 serves as a Doppler ultrasonic probe to emit Doppler measurement ultrasonic beam DB. An echo wave in response to ultrasonic beam DB is received by transducer 11.

Echo signals output from the ultrasonic transducer elements (a) in ultrasonic transducer 11 are input to and amplified by preamplifier 18 through switching circuit 12. The amplified echo signals from preamplifier 18 are delayed by reception delay circuit 20 by a delay time corresponding to the transmission delay time. The delayed signals are input to adder 21. An output signal from adder 21 is input to band-pass filter 24. In this case, since filter 24 has filter characteristics F1, the output signal from adder 21 is input as a Doppler signal to Doppler signal processor 25.

Doppler signal processing circuit 25 measures a Doppler frequency of the Doppler signal and outputs blood flow speed data. A method of measuring a blood flow speed from the Doppler signal is known to those skilled in the art. For example, Doppler frequency calculation is disclosed in U.S. patent application No. 888,510.

The blood flow speed signal from Doppler signal processing circuit 25 is input to digital scan converter 27 and converted into a television signal. The Doppler television signal from converter 26 is input to monitor 30 through adder 28. As shown in FIG. 6, blood flow speed image 44 is displayed together with the B-mode image. Line 42 on B-mode screen 31 shows the direction of Doppler beam DB and blood includes measurement point 43 thereon.

B-mode and Doppler images 41 and 44 displayed on monitor 30 can be visually observed to confirm immediately the position of the object to be examined and its blood flow state. The Doppler measurement direction 42 and the measurement point 43 can be changed by updating input information at control panel 23.

In the above embodiment, since the two-channel ultrasonic transducer is used, ultrasonic transmission/-reception can be performed at optimal frequencies to produce the B- and Doppler-mode images. The high-frequency components of the echo signals from the transducer correspond to the B-mode image signal, the low-frequency components correspond to the Doppler-mode image, and these components are selectively filtered through the filter having the corresponding filter characteristics. A signal having a high S/N ratio can be obtained in the Doppler mode, and an image signal having a high resolution can be obtained in the B mode. The arrangement of the transducer can be simplified by using the two-channel transducer, reliability of the transducer can be improved, maintenance procedures can be simplified, and the transducer can be easily handled since the transducer is made compact.

The type of transducer is not limited to a two-channel type, but the transducer can have three or more channels which are selectively switched. The filter circuit for filtering the B- and Doppler-mode image signals may comprise high- and low-pass filters.

Figure 7:
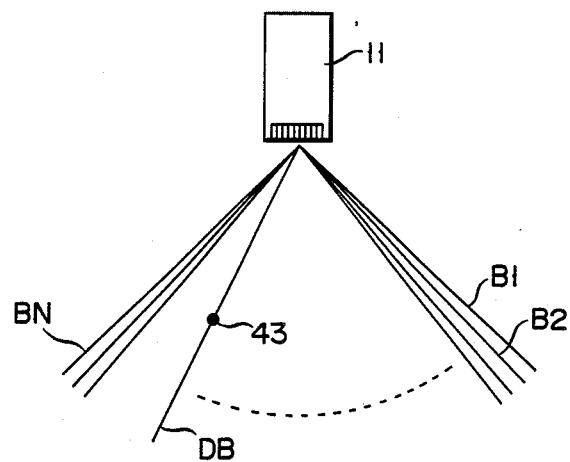
FIG. 7 is a view showing ultrasonic sector scanning by an ultrasonic transducer in an ultrasonic imaging apparatus according to another embodiment of the present invention.
Figure 8:
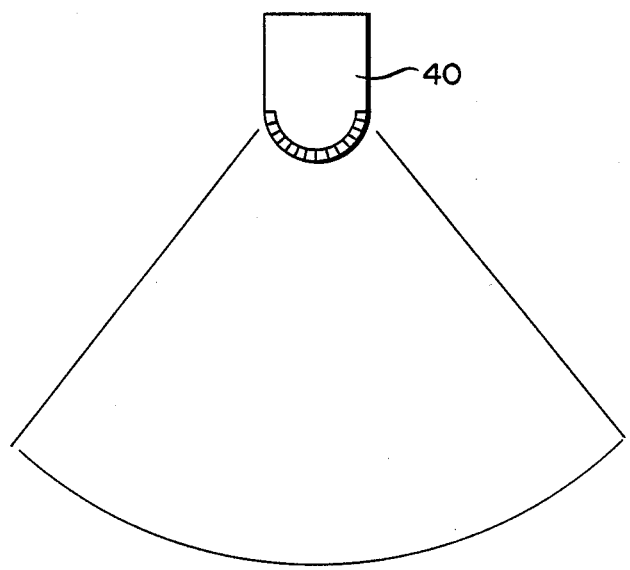
FIG. 8 is a view showing ultrasonic sector scanning by a convex type ultrasonic transducer.

The scan system for producing the B-mode image signal is not limited to the linear scan system, but can be replaced with a sector system as shown in FIGS. 7 and 8. The linear scan system is effective to image a portion (e.g., carotid observation) requiring selective observation. However, the sector scan system is effective for observation and imaging of a predetermined area such as a heart.

In operation of the ultrasonic imaging apparatus described above, the B mode and the Doppler mode can be alternately performed. In this case, in B-mode linear or sector scan, Doppler beam DB may be emitted for every line, and the B- and Doppler-mode image signals may be alternately produced. The switching timings of these signals can be determined in the program in CPU 22.

In order to increase the number of sampled signals of Doppler information, one-frame B-mode image data may be frozen in a frame memory, and sampling of Doppler information may be performed in the B-mode frozen state, thereby obtaining any sampling data and improving blood flow speed measurement precision.

In the Doppler mode, the Doppler ultrasonic beam is directed to a desired measurement point by changing beam radiation angle $\theta$. However, the transducer may be driven so as to change the ultrasonic transducer elements to be driven in the element array direction, so that the Doppler ultrasonic beam moves in the element array direction to pass through the desired measurement point.

FIG. 8 illustrates an apparatus using a convex type ultrasonic transducer 40. The convex type ultrasonic transducer 40 has a widen angle of a field of view so that deep and shallow areas can be widely observed.

What is claimed is:

1. An ultrasonic imaging apparatus comprising:
   an ultrasonic transducer, said transducer transmitting and receiving a high-frequency ultrasonic wave suitable for obtaining a B-mode image and a low-frequency ultrasonic wave suitable for obtaining a Doppler-mode image, said transducer outputting a high-frequency echo signal corresponding to the high-frequency ultrasonic wave and a low-frequency echo signal corresponding to the low-frequency ultrasonic wave;
   transmitting means for driving said ultrasonic transducer to output the high-frequency ultrasonic wave and the low-frequency ultrasonic wave therefrom;
   receiving means for processing the high-frequency echo signal and the low-frequency echo signal and for outputting a B-mode image signal and a Doppler-mode image signal; and
   display means for displaying the B-mode image signal and the Doppler-mode image signal output from said receiving means as the B-mode and Doppler-mode images,
   said ultrasonic transducer including
      a first piezo-electric ceramic having a center frequency $2f0$ that is twice resonance frequency and a thickness corresponding to about $\frac{1}{2}$ of the wavelength at the frequency $2f0$,
      a pair of electrodes formed on the front and rear surfaces of said first piezo-electric ceramic,
      a second piezo-electric ceramic formed on said electrode provided on said rear surface of said first piezo-electric ceramic and having the same thickness as that of said first piezo-electric ceramic,
      said first and second piezo-electric ceramics having only said pair of electrodes as their output leads
      an acoustic matching layer formed on said electrode formed on said front surface of said first piezo-electric ceramic and having a thickness corresponding to $\frac{1}{4}$ of a wavelength at the frequency $2f0$, and
      said first and second piezo-electric ceramics serving as a transducer having resonance frequency $2f0$ to output the high-frequency ultrasonic wave and said acoustic matching layer serving as a transducer having resonance frequency $f0$ to output the low frequency ultrasonic wave.

2. An apparatus according to claim 1, wherein said transmitting means comprises drive pulse output means for outputting a drive pulse delayed by delay time required for linear scan and a drive pulse delayed by delay time required for outputting a Doppler beam.

3. An apparatus according to claim 1, wherein said transmitting means comprises drive pulse output means for outputting a drive pulse delayed by delay time required for sector scan and a drive pulse delayed by delay time required for outputting a Doppler beam.

4. An apparatus according to claim 1, wherein said receiving means comprises signal processing circuit means for delaying the high- and low-frequency echo signals from said ultrasonic transducer means and outputting the B-mode image signal and the Doppler mode image signal, filter means for filtering the high- and low-frequency signals, and means for calculating a fluid flow speed from the low-frequency signal filtered through said filter means and for outputting fluid flow speed data.

5. An apparatus according to claim 1, wherein said transmitting means includes means for alternately driving said ultrasonic transducer means for at least every scanning line in the B and Doppler modes.

6. An apparatus according to claim 1, wherein said receiving means comprises means for holding a one-frame high-frequency signal and means for sampling the low-frequency signal in a holding period.

7. An apparatus according to claim 1, wherein said ultrasonic transducer means has a convex type ultrasonic transducer.

8. An apparatus according to claim 1, wherein said ultrasonic transducer means comprises a switching means for selectively switching said electrodes so that said first and second piezo-electric ceramics are selectively driven by said transmitting means, and transmitting the echo signals to said receiving means.

* * * * *